(12) United States Patent
Cason

(10) Patent No.: US 7,400,701 B1
(45) Date of Patent: Jul. 15, 2008

(54) BACKSCATTER INSPECTION PORTAL

(75) Inventor: W. Randall Cason, Danvers, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 11/097,092

(22) Filed: Apr. 1, 2005

Related U.S. Application Data

(60) Provisional application No. 60/561,079, filed on Apr. 9, 2004.

(51) Int. Cl.
*G01N 23/201* (2006.01)
*G01N 23/203* (2006.01)

(52) U.S. Cl. ............................... 378/57; 378/87; 378/88

(58) Field of Classification Search .................... 378/57, 378/86–90, 146, 9, 19
See application file for complete search history.

(56) References Cited

U.S. PATENT DOCUMENTS

| | | | | |
|---|---|---|---|---|
| 4,799,247 A * | 1/1989 | Annis et al. | .................... | 378/87 |
| 5,181,234 A * | 1/1993 | Smith | .......................... | 378/87 |
| 5,638,420 A * | 6/1997 | Armistead | .................... | 378/57 |
| 5,696,806 A * | 12/1997 | Grodzins et al. | ............. | 378/86 |
| 5,930,326 A * | 7/1999 | Rothschild et al. | ............ | 378/57 |
| 6,018,562 A * | 1/2000 | Willson | .......................... | 378/9 |
| 6,081,580 A * | 6/2000 | Grodzins et al. | ............... | 378/87 |
| 6,094,472 A | 7/2000 | Smith | .......................... | 378/86 |
| 6,151,381 A * | 11/2000 | Grodzins et al. | ............... | 378/90 |
| 6,192,104 B1 * | 2/2001 | Adams et al. | .................. | 378/90 |
| 6,212,251 B1 * | 4/2001 | Tomura et al. | ................. | 378/15 |
| 6,249,567 B1 | 6/2001 | Rothschild et al. | ........... | 378/88 |
| 6,421,420 B1 * | 7/2002 | Grodzins | .................... | 378/98.6 |
| 6,442,233 B1 * | 8/2002 | Grodzins et al. | ............... | 378/57 |
| 6,459,761 B1 | 10/2002 | Grodzins et al. | ............... | 378/57 |
| 6,473,487 B1 * | 10/2002 | Le | ............... | 378/57 |
| 6,556,653 B2 * | 4/2003 | Hussein | .......................... | 378/90 |
| 6,567,496 B1 * | 5/2003 | Sychev | .......................... | 378/57 |
| 6,876,719 B2 * | 4/2005 | Ozaki | .......................... | 378/7 |
| 6,879,657 B2 * | 4/2005 | Hoffman | ........................ | 378/7 |
| 7,103,137 B2 * | 9/2006 | Seppi et al. | .................... | 378/9 |

FOREIGN PATENT DOCUMENTS

WO    WO 98/02763    1/1998

\* cited by examiner

*Primary Examiner*—Allen C. Ho
(74) *Attorney, Agent, or Firm*—Bromberg & Sunstein LLP

(57) ABSTRACT

A system and method for inspecting an object with multiple sources of penetrating radiation. Irradiation of the inspected object by the sources is temporally sequenced such that the source of detected scattered radiation is unambiguous. Thus, multiple views of the inspected object may be obtained and image quality may be enhanced, even in a compact geometry in which the beams are substantially coplanar.

13 Claims, 3 Drawing Sheets

BACKSCATTER INSPECTION PORTAL

The present application claims priority from U.S. Provisional Application No. 60/561,079, filed Apr. 9, 2004, which is incorporated herein by reference.

TECHNICAL FIELD

The present invention relates to systems and methods for inspecting objects with penetrating radiation, and, more particularly, the invention relates to inspection systems employing multiple sources of radiation.

BACKGROUND ART

It is desirable to determine the presence of objects, such as contraband, weapons, or explosives, that have been concealed, for example, in a moving vehicle, or on a person, or in any inspected object, while the inspected object is moved past one or more systems that image the contents of the object using penetrating radiation. The determination should be capable of being made while the inspected object is in motion, or, alternatively, while the inspection system is in motion with respect to the inspected person or object. Indeed, since inspection rate, and thus hourly throughput, is at a premium, it is desirable that the vehicle, for example, be driven without requiring the driver or passengers to alight. In case a detection is made, a visual image should be available for verification.

The use of images produced by detection and analysis of penetrating radiation scattered from an irradiated object, container, or vehicle is the subject, for example, of U.S. Pat. No. 6,459,764, to Chalmers et al. (the "Chalmers patent"), issued Oct. 1, 2002, and incorporated herein by reference. The Chalmers patent teaches backscatter inspection of a moving vehicle by illuminating the vehicle with x-rays from above or beneath the moving vehicle, as well as from the side.

The use of an x-ray source and an x-ray detector, both located in a portal, for purposes of screening personnel, is the subject, for example, of U.S. Pat. No. 6,094,472, to Smith, issued Jul. 25, 2000.

X-rays are scattered from matter in all directions, therefore, scatter may be detected by an x-ray detector disposed at any angle to the scattering material with respect to the direction of incidence of the illuminating radiation. Therefore, a "flying spot" irradiation system is typically used, whereby a single point on the inspected object is illuminated with penetrating radiation at any given moment, so that the locus of scatter can be determined unambiguously, at least with respect to the plane transverse to the direction of the beam of penetrating radiation.

In order to obtain multiple views of an inspected object, multiple backscatter imaging systems may be employed in a single inspection tunnel. This may result in interference, or cross-talk, between respective imaging systems, resulting in image degradation. This is due to the lack of each flying-spot imager's ability to distinguish the origin of the scattered radiation from each imager's source. To date, this problem has been addressed by placing the imagers some distance apart to minimize cross talk. This approach causes the size of the overall system to increase. In space-limited applications, this is often undesirable.

SUMMARY OF THE INVENTION

In one embodiment of the present invention, there is provided an inspection system for inspecting an object that is characterized by motion in a particular direction with respect to the inspection system, by virtue of motion with respect to the local frame of reference of either the object, the inspection system, or both. The inspection system has a first source for providing a first beam of penetrating radiation of specified cross-section directed in a first beam direction substantially transverse to the direction of motion of the object. It also has a second source for providing a second beam of penetrating radiation in a second beam direction, and may have additional sources of additional beams. The beams of penetrating radiation are temporally interspersed. Additionally, the system has a plurality of scatter detectors for detecting radiation scattered from at least one of the first beam and the other beams by any scattering material within the inspected object and for generating a scattered radiation signal. The system may also have one or more transmission detectors for detecting penetrating radiation transmitted through the object. Finally, the system has a controller for creating an image of the scattering material based at least on the scattered radiation signal or for otherwise characterizing the scattering material.

In accordance with alternate embodiments of the invention, the first source of penetrating radiation may be an x-ray source, as may the other sources of penetrating radiation. The first beam direction and the direction of any other beam may be substantially coplanar. The various sources may include a beam scanning mechanism, such as a rotating chopper wheel or an electromagnetic scanner, and one or more of the beams may be pencil beams.

In accordance with yet further embodiments of the invention, emission of penetrating radiation in the first beam may be characterized by a first temporal period and emission of penetrating radiation in the second beam may be characterized by a second temporal period, the first and the second temporal periods offset by fixed phase relationship. The temporal period of each source may be characterized by a duty cycle, and the emission of adjacent sources may be characterized by a phase relationship with respect to an adjacent source, where the phase relationship may equal to $2\pi$ times the duty cycle.

In accordance with yet further embodiments of the invention, the inspection system may further including a display for displaying a scatter image of material disposed within the inspected object.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In accordance with embodiments of the present invention, beam cross talk is minimized between or among multiple flying-spot backscatter imaging systems configured as a multi-view backscatter inspection system, with no restriction on the distance between the individual imaging systems. In other words, in a multi-view system comprised of individual backscatter imaging systems for each view, the individual imaging systems can be placed as close together as is physically possible, while cross talk is advantageously reduced or eliminated.

Figure 3:
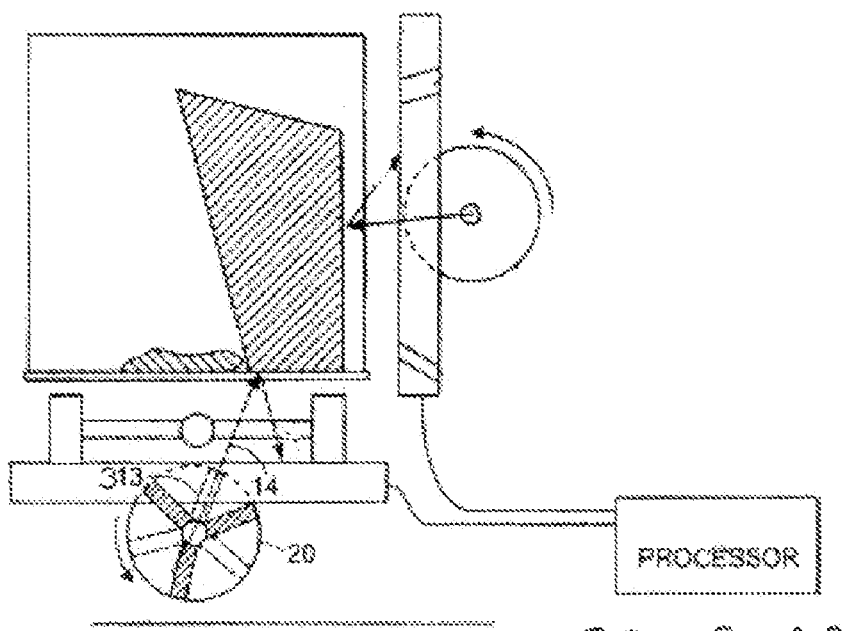
FIG. 3 shows a prior art backscatter system employing a rotating chopper wheel of a sort employed in various embodiments of the present invention.

Methods and advantages of backscatter inspection of a moving vehicle by illuminating the vehicles with x-rays from either above or beneath the moving vehicle are described in U.S. Pat. No. 6,249,567, issued Jun. 19, 2001, which is incorporated herein by reference. In an embodiment of the aforesaid patent, illustrated in FIG. 3, rotating chopper wheel 20 is used to develop a pencil beam 14 which may be swept in a plane substantially parallel to that of the page. The formation of pencil beam 14 by a series of tubular collimators 313 distributed as spokes on rotating wheel 20 is known in the art. In accordance with preferred embodiments of the present invention, regions of enhanced backscatter that arise due to materials concealed close to the side walls of a vehicle are revealed without requiring that penetrating radiation traverse the vehicle during the course of inspection.

Figure 1:
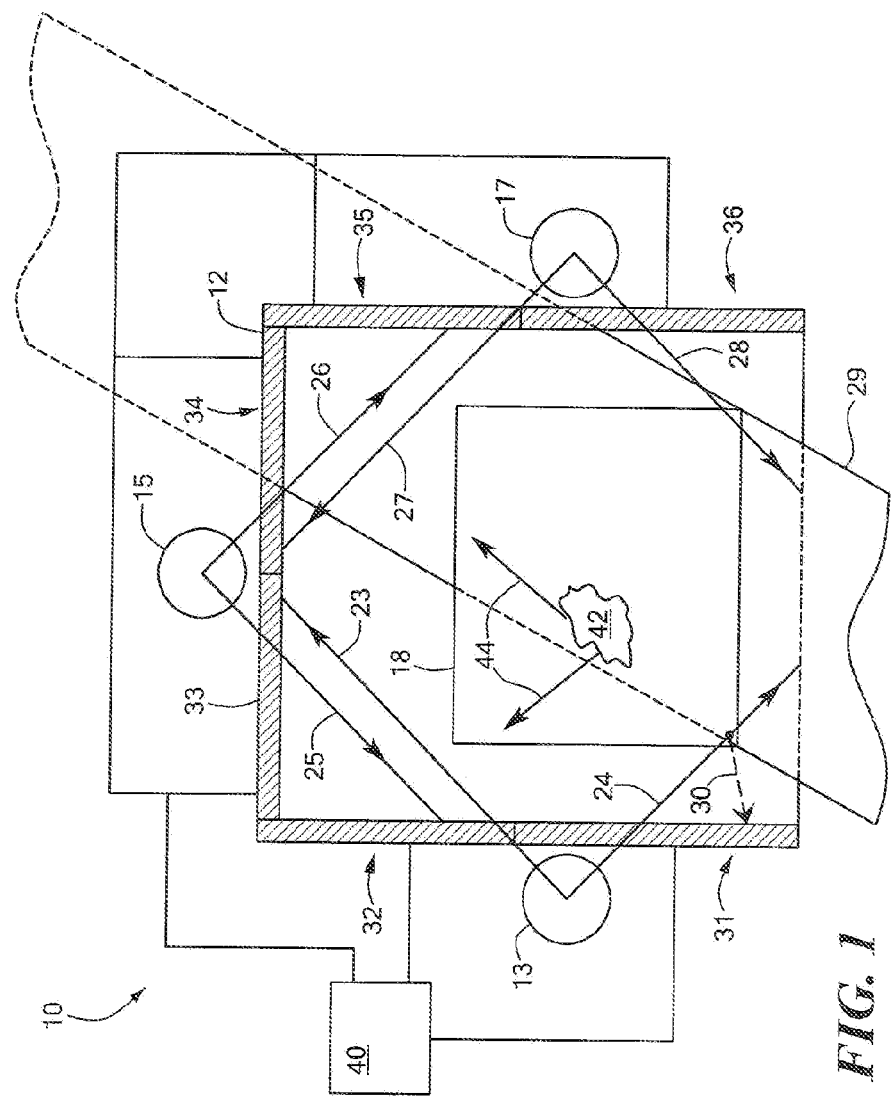
FIG. 1 shows a schematic cross sectional view of an x-ray inspection system that uses multiple backscatter imaging systems in accordance with embodiments of the present invention.

FIG. 1 shows a schematic cross-sectional view of the elements of an inspection system, designated generally by numeral 10. An object of inspection 18, which may be animate or inanimate, moves, or is moved, in a direction into, or out of, the page and thus traverses a portal 12. Portal 12 supports a plurality of sources 13, 15, and 17 of penetrating radiation. Sources 13, 15, and 17 are typically x-ray tubes having beam forming and steering mechanisms known in the art. For example, source 13 emits penetrating radiation in a beam 23 having a cross-section of a specified shape. For scatter imaging applications, a narrow pencil beam is typically employed. Beam 23 of penetrating radiation, may be, for example, a beam of x-rays such as a polychromatic x-ray beam. While source 13 of penetrating radiation is preferably an x-ray tube, for example, however other sources of penetrating radiation, such as a linac (linear accelerator), are within the scope of the present invention, and, indeed, the penetrating radiation is not limited to x-ray radiation and may include gamma ray radiation.

A scanning mechanism is provided for scanning beam 23 along a substantially vertical axis, such that, during a portion of a duty cycle, beam 23 is directed in a series of directions such as 24. Object 18 that is to be inspected moves past beam 23 in a substantially horizontal direction, into the page, in the depiction of FIG. 1. In alternate embodiments of the invention, the source and/or other portions of the inspection system may be moved in relation to object 18, which may be moving itself, or stationary.

Figure 4:
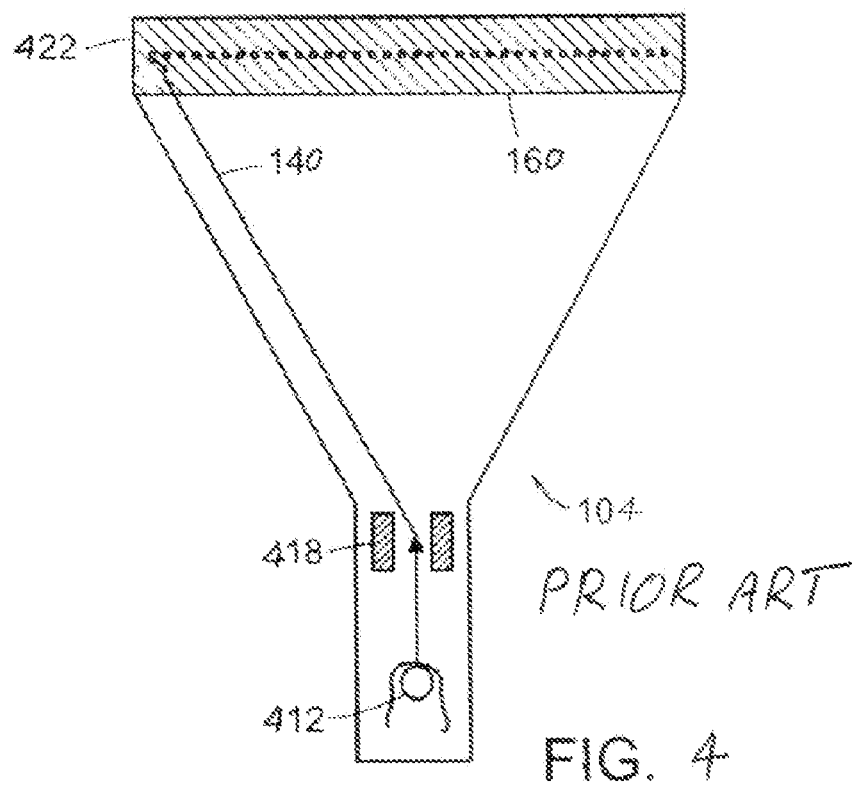
FIG. 4 shows a prior art backscatter system employing an electromagnetic scanner of a sort employed in various embodiments of the present invention.
Figure 1:
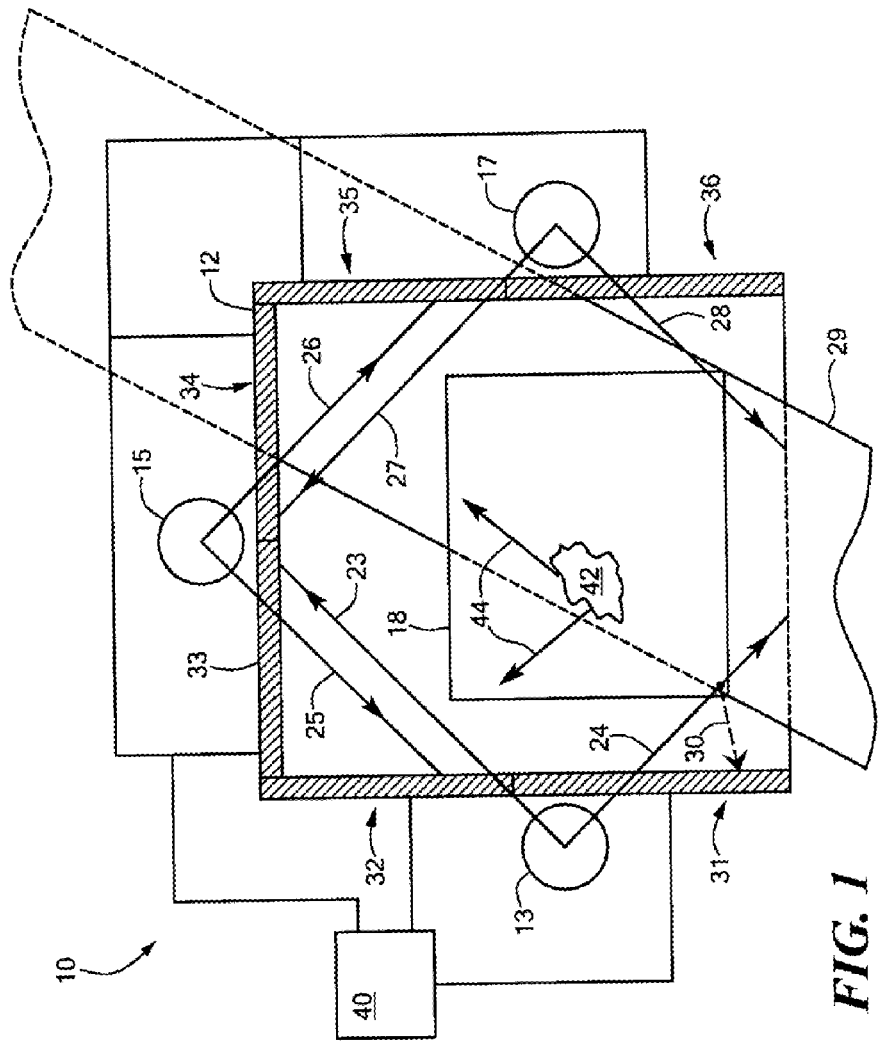
Figure 2:
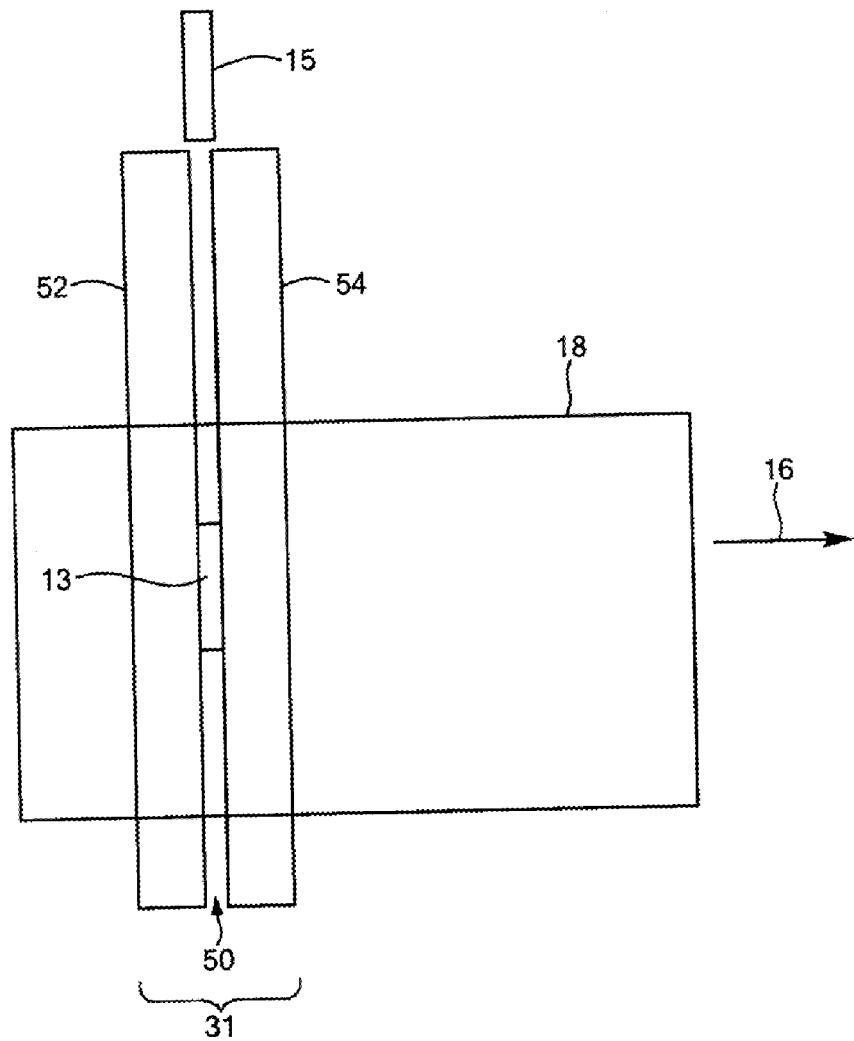
Figure 3:
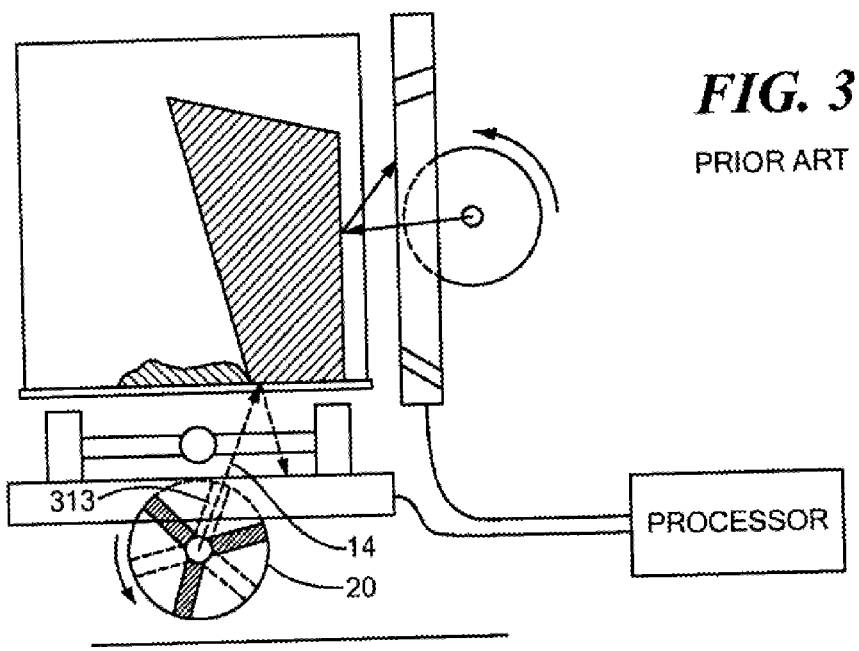
Figure 4:
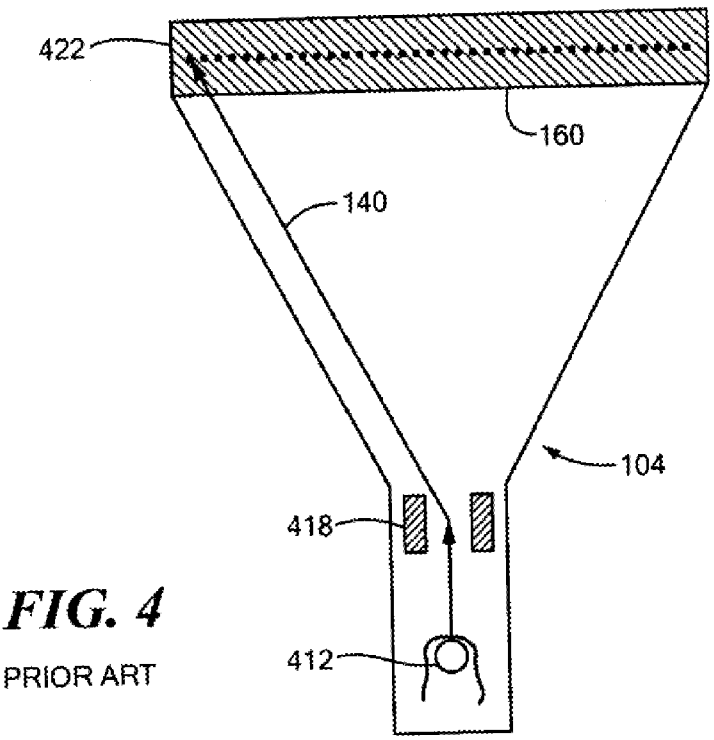

Source 13 may include a scanning mechanism such as a flying spot rotating chopper wheel 20 (shown in FIG. 3) as known to persons skilled in the art. Alternatively, electromagnetic scanners may be employed, such as scanner 104 (shown in FIG. 4) described in U.S. Pat. No. 6,421,420, issued July 23, 2002 and entitled "Method and Apparatus for Generating Sequential Beams of Penetrating Radiation," which is incorporated herein by reference. A source 412 supplies a beam of charged particles 140 that are accelerated to a surface of a target 160. Electromagnetic beam director 418 can be any electromagnetic beam directing arrangement such as magnetic or electrostatic yokes. Penetrating electromagnetic radiation is emitted by target 160 and pass through a collimator 422 disposed a specified distance from the target, thus producing sequential parallel beams of radiation.

Beams of sources 15 and 17 are shown in typical extremal positions of their respective scans, and are labeled 25, 26, 27, and 28. Inspected object 18, which, as discussed, may refer to a vehicle, a container, or a person, for example, may be self-propelled through beams 23-28 or may be conveyed by a mechanized conveyor 29 or pulled by a tractor, etc. In alternate embodiments of the invention, the inspection system, configured, for example, as a portal, may move, or be moved, over an object such as a vehicle that may, itself, be moving or stationary.

Beams 23-28 will be referred to in the present description, without limitation, as x-ray beams. In accordance with preferred embodiments of the invention, a rotating chopper wheel is used to develop a pencil beam 23-28 which may be swept in a plane substantially parallel to that of the page. The cross section of pencil beam 23 is of comparable extent in each dimension and is typically substantially circular, although it may be many shapes. The dimensions of pencil beam 23-28 typically define the scatter image resolution which may be obtained with the system. Other shapes of beam cross section may be advantageously employed in particular applications.

A detector arrangement, typified by scatter detector 31, is disposed in a plane parallel to the direction of motion of object 18 during the course of the scan. X-rays 30 scattered by Compton scattering out of beam 24 in an essentially backward direction are detected by one or more backscatter detectors 31 disposed between source 13 and object 18. Additional detector arrangements 32, 33, 34, 35, and 36 may be used supplementarily for detecting x-rays Compton-scattered from beam 24 and similarly, as will presently be described, for each of the other beams incident, in turn, on inspected object 18.

Additionally, transmission detectors disposed distally to the inspected object 18 with respect to the emitting source may be used to augment the scatter image or images with an image of the object as obtained in transmitted x-rays, for example, the detector elements designated 35 and 36 detect the emission of source 13 as transmitted through the inspected object. In another embodiment of the invention, a single separate detector is disposed between the pair of scatter detectors 35 and the pair of scatter detectors 36 and is employed for detection of penetrating radiation transmitted through object 18.

Within the scope of the invention, any x-ray detection technology known in the art may be employed for the detector arrangements 31-36. The detectors may be scintillation materials, either solid or liquid or gaseous, viewed by photosensitive detectors such as photomultipliers or solid state detectors. Liquid scintillators may be doped with tin or other element or elements of high atomic number. Respective output signals from the scatter detectors 31-36 are transmitted to a processor 40, and processed to obtain images of feature 42 inside the inspected object 18. Since incident x-ray photons are scattered by scattering sources within object 18 into all directions, detectors with large areas are used to maximize the collection of the scattered photons. In accordance with certain embodiments of the invention, processor 40 (otherwise referred to herein as a 'controller') may also be employed to derive other characteristics of the scattering object, such as its mass, mass density, effective atomic number, etc., all as known in the art.

In order to allow views of the inspected object from multiple directions, multiple sources 13-17 are used to irradiate the inspected object. However, since the photons emitted by each source are scattered in all directions, care must be exercised in order to eliminate cross-talk, i.e., the misidentification of the source of irradiation. In accordance with embodiments of the present invention, cross talk is advantageously reduced or eliminated by ensuring that only one source is emitting radiation at a time. First, the duty-cycle of the beams emitted from the imaging systems is set less-than or equal-to the inverse of the number of imaging systems, or views, in the multi-view system. For example, if the number of views desired is six, each imaging system is set for a duty cycle of 1/6, or less.

Next, the phase relationship between each pair of adjacent sources is set to $2\pi$ times the duty cycle. This results in sequenced radiation emission from the imagers, eliminating the possibility of concurrent emission from more than one imager. For example, a multi-view inspection system with 6 sources would require that they run at the same frequency, that their duty-cycles be 1/6, and that their phase relationship be $2\pi/6$, or 60 degrees.

In cases where flying-spot systems are realized by mechanical means such as rotating hoops and chopper wheels, these aforesaid criteria may be met by synchronization of the motion of the mechanical chopper elements, biased by phase offsets. Thus, for example, where collimators are rotated to define the path of emergent x-ray beam 23, close-loop motion controller systems known in the art may be employed to drive the rotation of the collimators. The duty cycle is controlled by setting the fan aperture (the total sweep angle of a beam, i.e., the angle between extremal beams 23 and 24 of a single source), equal to $2\pi$ times the duty cycle. In systems where the emitted radiation can be controlled electronically, any desired sequence of irradiation or range of sweep may be set, without limitation, entirely by electronic or software control.

By virtue of temporal sequencing which reduces or eliminates cross-talk, sources may be placed in greater proximity than otherwise possible. In particular, sources 13-17 may be disposed in a single plane, which advantageously permits virtually simultaneous on/off control of the x-rays regardless of the speed with which the object is passing by the imagers.

The system described may advantageously provide for an image to be derived from the perspective of each successive source 13-17. FIG. 1 shows an exemplary three-view system, with beams 23, 25, etc. each sweeping trajectories that are coplanar.

The beams from each source sweep in sequence, such that no more than one source is emitting radiation at a time. Thus, source (or 'imager') 13 sweeps its beam first. Radiation scattered from the object, as represented by rays 44 is received by all of the detectors. The signals from each of the detectors are acquired as separate channels by an acquisition system. This process is repeated for each of the three imagers, creating "slices" of the object as it moves by.

Figure 2:
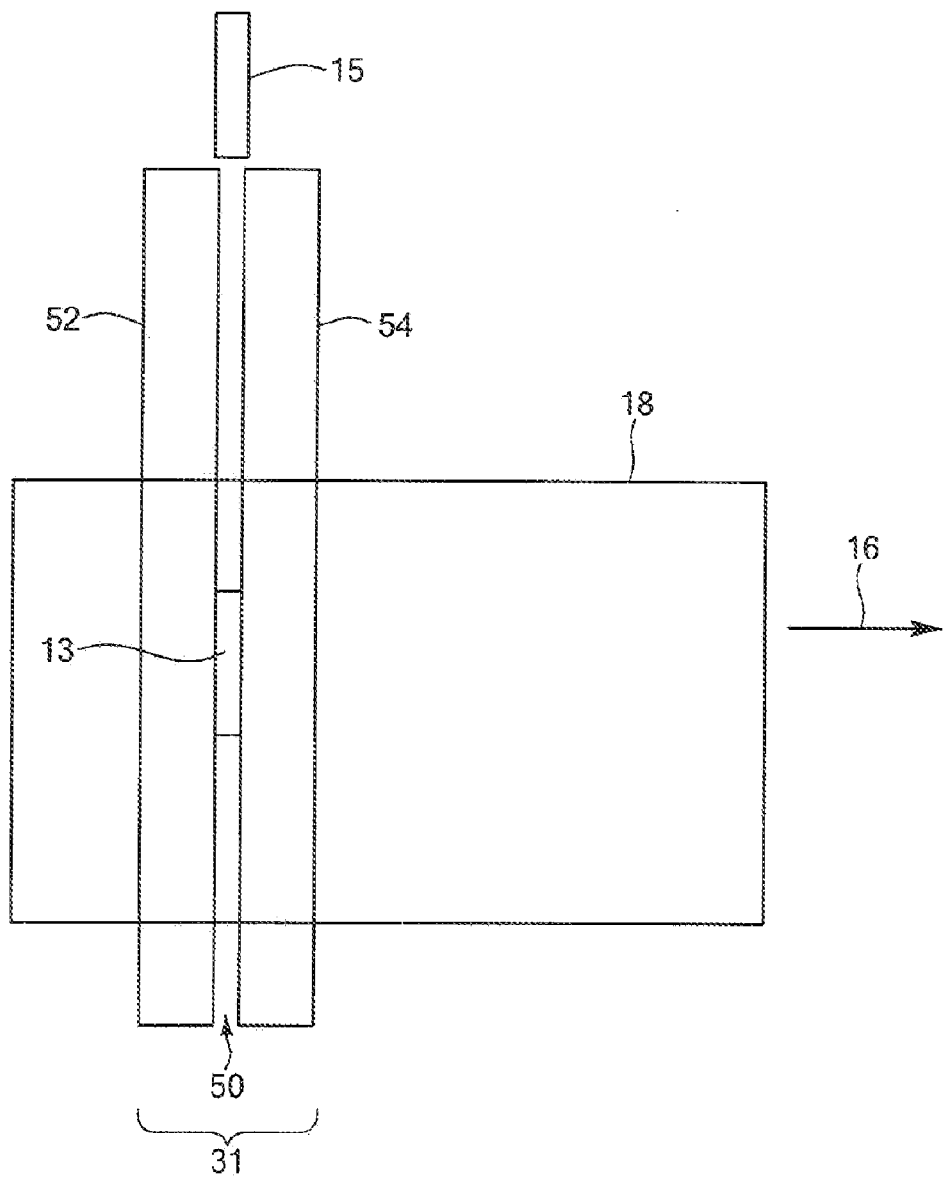
FIG. 2 shows a side view of the x-ray inspection system embodiments of FIG. 1.

Referring now to FIG. 2, a side view is shown of the arrangement of FIG. 1, with elements designated by corresponding numbers. A slot 50 is shown through which the beam of source 13 passes through segments 52 and 54 of detector 31 as object 18 is scanned while moving in a lateral direction 16.

The signals from the detectors can be selectively used to reconstruct an image of the object. Since scattered photons 44 detected by detectors 33 and 34 from source 13 are as useful as scattered photons from source 17, these same detectors can be shared among all sources, and result in improved scatter collection with efficient use of the detector hardware.

Embodiments of this invention, furthermore, may advantageously allow multi-view Flying-Spot X-ray Scatter imaging to be practiced in a smaller operational footprint by eliminating cross talk, and by allowing closer positioning of the individual imagers for each view. The close positioning of these imagers (where an "imager" refers to a source, at least one detector, and associated electronics and signal processing) may also allow sharing of scatter detectors between, or among, imagers, allowing more scatter collection for improved image quality, with efficient use of detector hardware.

In applications where scanning of selective regions of the object is desired, co-planar positioning of the imagers allows simultaneous on/off control of the x-rays regardless of the speed with which the object is passing by the imagers. This greatly simplifies the design of the control of x-ray emissions from each imager in the multi-view inspection system, thus individual sequencing of x-ray emissions need not be performed as is typically practiced in systems in which emission is not co-planar.

Besides imaging contents of concealing enclosures, in terms of which embodiments of the present invention have been described, other characteristics of inspected objects may be obtained within the scope of the present invention. For example, backscatter techniques may be applied, as known in the art, for deriving mass, mass density, mass distribution, mean atomic number, or likelihood of containing targeted threat material.

In accordance with certain embodiments of the invention, x-rays having maximal energies in the range between 160 keV and 300 keV are employed. At this energy, x-rays penetrate into a vehicle, and organic objects inside the Vehicle can be detected. Since lower doses of x-ray irradiation are thus possible, automobiles may be scanned using the present invention. For applications where the scanned vehicle may contain personnel, end point energies below 300 keV are preferred. The scope of the present invention, however, is not limited by the range of penetrating photons employed.

The described embodiments of the invention are intended to be merely exemplary and numerous variations and modifications will be apparent to those skilled in the art. All such variations and modifications are intended to be within the scope of the present invention as defined in the appended claims.

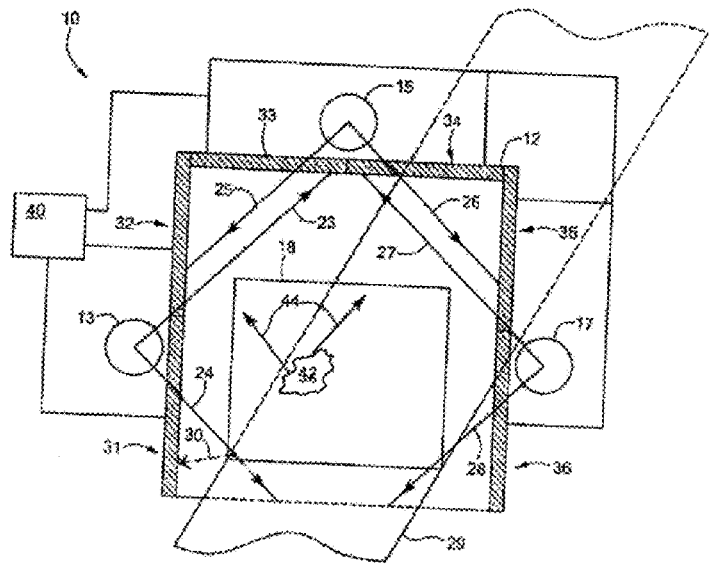

What is claimed is:

1. An inspection system for inspecting an object characterized by motion in a direction with respect to the inspection system, the system comprising:
   a. a first pencil-beam source for providing a first beam of penetrating radiation of specified cross-section directed in a first beam direction substantially transverse to the direction of motion of the object;
   b. a second pencil-beam source for providing a second beam of penetrating radiation of specified cross-section substantially coplanar with, and substantially perpendicular to, the first beam of penetrating radiation, directed in a second beam direction, and temporally interspersed with the first beam of penetrating radiation;
   c. a plurality of scatter detectors each scatter detector of which is disposed so as to detect radiation scattered from both the first beam and the second beam by any scattering material within the inspected object and for generating a scattered radiation signal; and
   d. a controller for creating an image of the scattering material based solely on the scattered radiation signal.

2. The inspection system as set forth in claim 1, wherein the inspection system is spatially fixed.

3. The inspection system as set forth in claim 1, wherein the first source of penetrating radiation is an x-ray source.

4. The inspection system as set forth in claim 1, wherein the first source of penetrating radiation includes a beam scanning mechanism.

5. The inspection system as set forth in claim 4, wherein the beam scanning mechanism is a rotating chopper wheel.

6. The inspection system as set forth in claim 4, wherein the beam scanning mechanism includes an electromagnetic scanner.

7. The inspection system as set forth in claim 1, wherein emission of penetrating radiation in the first beam is characterized by a first temporal period and emission of penetrating radiation in the second beam is characterized by a second temporal period, the first and the second temporal periods offset by fixed phase relationship.

8. The inspection system as set forth in claim 7, wherein the temporal period of each source is characterized by a duty cycle.

9. The inspection system as set forth in claim 8, wherein the temporal period of each source is characterized by phase relationship with respect to an adjacent source equal to $2\pi$ times the duty cycle.

10. The inspection system as set forth in claim 1, further comprising at least one transmission detector for detecting at least one of the first beam and the second beam as transmitted through the inspected object and for generating a transmitted radiation signal.

11. A method for inspecting an object, the method comprising:
    a. illuminating the object with penetrating radiation formed into a first pencil beam;
    b. illuminating the object with penetrating radiation formed into a second pencil beam, the second pencil beam substantially coplanar with the first pencil beam, at a fixed and substantially perpendicular orientation with respect to the first pencil beam, and temporally interspersed with respect to the first pencil beam;
    c. detecting radiation from the first pencil beam and the second pencil beam
        scattered by the object with at least one detector that detects scattering from both the first and the second pencil beams to generate a scattered radiation signal; and
    d. imaging the object solely on the basis of the scattered radiation signal.

12. A method according to claim 11, further including:
    e. varying the orientation of the first pencil beam with respect to the object.

13. A method according to claim 11, further including:
    e. displaying a scatter image of the scattered radiation signal.

* * * * *

UNITED STATES PATENT AND TRADEMARK OFFICE
CERTIFICATE OF CORRECTION

PATENT NO.         : 7,400,701 B1
APPLICATION NO. : 11/097092
DATED              : July 15, 2008
INVENTOR(S)        : W. Randall Cason It is certified that error appears in the above-identified patent and that said Letters Patent is hereby corrected as shown below:

The title page, showing an illustrative figure, should be deleted and substitute therefor the attached title page.

Delete drawing sheets 1 - 3, and substitute therefor the drawing sheets, consisting of FIGS. 1-4, as shown on the attached pages.

Signed and Sealed this

Twenty-first Day of October, 2008

JON W. DUDAS
*Director of the United States Patent and Trademark Office*

(12) United States Patent
Cason

(10) Patent No.: US 7,400,701 B1
(45) Date of Patent: Jul. 15, 2008

(54) BACKSCATTER INSPECTION PORTAL

(75) Inventor: W. Randall Cason, Danvers, MA (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 11/097,092

(22) Filed: Apr. 1, 2005

Related U.S. Application Data

(60) Provisional application No. 60/561,079, filed on Apr. 9, 2004.

(51) Int. Cl.
G01N 23/201 (2006.01)
G01N 23/203 (2006.01)

(52) U.S. Cl. .................. 378/57; 378/87; 378/88

(58) Field of Classification Search ............ 378/57, 378/86–90, 146, 9, 19
See application file for complete search history.

(56) References Cited

U.S. PATENT DOCUMENTS

| | | | | |
|---|---|---|---|---|
| 4,799,247 A * | 1/1989 | Annis et al. | | 378/87 |
| 5,181,234 A * | 1/1993 | Smith | | 378/87 |
| 5,638,420 A * | 6/1997 | Armistead | | 378/57 |
| 5,696,806 A * | 12/1997 | Grodzins et al. | | 378/86 |
| 5,930,326 A * | 7/1999 | Rothschild et al. | | 378/57 |
| 6,018,562 A * | 1/2000 | Willson | | 378/9 |
| 6,081,580 A * | 6/2000 | Grodzins et al. | | 378/87 |
| 6,094,472 A | 7/2000 | Smith | | 378/86 |
| 6,151,381 A * | 11/2000 | Grodzins et al. | | 378/90 |
| 6,192,104 B1 * | 2/2001 | Adams et al. | | 378/90 |
| 6,212,251 B1 * | 4/2001 | Tomura et al. | | 378/15 |
| 6,249,567 B1 | 6/2001 | Rothschild et al. | | 378/88 |
| 6,421,420 B1 * | 7/2002 | Grodzins | | 378/98.6 |
| 6,442,233 B1 * | 8/2002 | Grodzins et al. | | 378/57 |
| 6,459,761 B1 | 10/2002 | Grodzins et al. | | 378/57 |
| 6,473,487 B1 * | 10/2002 | Le | | 378/57 |
| 6,556,653 B2 * | 4/2003 | Hussein | | 378/90 |
| 6,567,496 B1 * | 5/2003 | Sychev | | 378/57 |
| 6,876,719 B2 * | 4/2005 | Ozaki | | 378/7 |
| 6,879,657 B2 * | 4/2005 | Hoffman | | 378/7 |
| 7,103,137 B2 * | 9/2006 | Seppi et al. | | 378/9 |

FOREIGN PATENT DOCUMENTS

WO    WO 98/02763    1/1998

* cited by examiner

*Primary Examiner*—Allen C. Ho
(74) *Attorney, Agent, or Firm*—Bromberg & Sunstein LLP

(57) ABSTRACT

A system and method for inspecting an object with multiple sources of penetrating radiation. Irradiation of the inspected object by the sources is temporally sequenced such that the source of detected scattered radiation is unambiguous. Thus, multiple views of the inspected object may be obtained and image quality may be enhanced, even in a compact geometry in which the beams are substantially coplanar.

13 Claims, 3 Drawing Sheets